US00PP36742P3

(12) United States Plant Patent
Gmitter, Jr.

(10) Patent No.: US PP36,742 P3
(45) Date of Patent: Jun. 17, 2025

(54) LEMON PLANT NAMED 'CE-D5-1-9-42'

(50) Latin Name: *Citrus limon.*
Varietal Denomination: CE-D5-1-9-42

(71) Applicant: Florida Foundation Seed Producers, Inc., Marianna, FL (US)

(72) Inventor: Frederick Gmitter, Jr., Lakeland, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/751,529

(22) Filed: Jun. 24, 2024

(65) Prior Publication Data

US 2025/0008853 P1 Jan. 2, 2025

Related U.S. Application Data

(60) Provisional application No. 63/510,537, filed on Jun. 27, 2023.

(51) Int. Cl.
*A01H 5/08* (2018.01)
*A01H 6/78* (2018.01)

(52) U.S. Cl.
USPC ..... Plt./201
CPC ..... *A01H 6/785* (2018.05)

(58) Field of Classification Search
USPC ..... Plt./201
CPC ..... A01H 6/785; A01H 5/08
See application file for complete search history.

*Primary Examiner* — Keith O. Robinson
(74) *Attorney, Agent, or Firm* — Koenig IP Works, PLLC; Katherine Koenig

(57) ABSTRACT

A new and distinct cultivar of lemon plant named 'CE-D5-1-9-42', characterized by nearly seedless fruit, early fruiting, and high fruit production. Additionally, the new lemon cultivar also is compatible with trifoliate orange rootstocks, unlike most lemon varieties. This new cultivar has high quality fresh fruit, as well as juice, peel oil, and other lemon by-products viable for processing. Further, given the new lemon cultivar's good HLB tolerance typical of lemons, and its near seedlessness, this new cultivar may have significant dooryard tree potential.

20 Drawing Sheets

Genus and species: *Citrus limon.*
Cultivar denomination: 'CE-D5-1-9-42'.

ACKNOWLEDGEMENT OF FEDERAL RESEARCH SUPPORT

N/A.

BACKGROUND OF THE NEW CULTIVAR

The present invention relates to a new and distinct cultivar of lemon, botanically known as *Citrus limon* and hereinafter referred to by the name 'CE-D5-1-9-42'.

The new lemon cultivar 'CE-D5-1-9-42' arose as an irradiated budwood clone from 'Cook Eureka' lemon (not patented), produced as part of a large project to generate lemon clones that could produce higher yields of good quality peel oil for industrial use. The original tree was planted in Fort Pierce in 1999. The new cultivar 'CE-D5-1-9-42' was among a second group of clones selected for high oil production and was included in a large field trial planted in South America under a materials transfer agreement (MTA) with a local farm in 2013. Pathogen-tested budwood was sent there, where it went through quarantine and further testing, for propagation onto multiple rootstocks including 'Flying Dragon' (not patented). Among 11 clones identified in the trial to be nearly seedless, higher young-tree production was observed on trees of 'CE-D5-1-9-42' on 'Flying Dragon' rootstock than with the other clones. Trueness-to-type was demonstrated by additional trees propagated on Afghan sour orange rootstock (not patented) and experimental rootstock hybrid '46x20-04-6' (not patented) and planted in Fellsmere, Florida.

Plant Breeder's Rights for this cultivar have not been applied for. The new lemon cultivar 'CE-D5-1-9-42' has not been made publicly available more than one year prior to the priority filing date of this application.

SUMMARY OF THE INVENTION

The new lemon cultivar 'CE-D5-1-9-42' has not been observed under all possible environmental conditions. The phenotype of the new cultivar may vary with variations in environment and cultural practices such as temperature, light intensity, fertilization, irrigation, and application of plant growth regulators without any change in genotype.

A new and distinct nearly seedless true lemon, which was originally selected for high peel oil production. The new cultivar 'CE-D5-1-9-42' was selected as a candidate for release based on its high early fruit production and near seedlessness. This cultivar can bring greater fresh fruit value to lemons grown in Florida, as well as good value in processing for juice, peel oil, and other lemon by-products. Further, with good *Citrus* huanglongbing or greening (HLB) tolerance found in lemons, and its near seedlessness, this lemon cultivar may also have significant dooryard tree potential.

The new cultivar 'CE-D5-1-9-42' was identified as a seedless clone in the trial in Bolivia in 2017, where zero seed were found in 30 fruit. Subsequent seed counts show that most fruit are seedless, but a small percentage of fruit can have one or two small seeds. Fruit with more than two seeds have been observed, but this occurrence is very rare. This level of seedlessness is comparable to low-seeded lemon clones now finding favor in the domestic and international fresh fruit markets. Fruit appearance, fragrance, and juice content are typical of 'Eureka' lemon clones. Proprietary analyses of peel oil quality conducted in Tucuman, Argentina, concluded that the oils were commercially acceptable. Thus, this selection has good potential for fresh fruit or processed lemons grown in Florida, as well as for the door yard lemon tree market.

Most 'Eureka' lemon clones are incompatible with trifoliate orange rootstocks, so the good performance on 'Flying Dragon' (a trifoliate orange variety), with no indications of incompatibility, is surprising; if it holds true on other trifoliate orange rootstocks and hybrids, this would be a unique and quite valuable attribute. 'Flying Dragon' rootstock is widely used in the Tucuman lemon growing region for critical tree size control, but 'Eureka' lemons cannot be grown on 'Flying Dragon' rootstock there because of the incompatibility.

The new cultivar 'CE-D5-1-9-42' is distinguishable from 'Eureka' lemons in that 'CE-D5-1-9-42' has not shown any graft incompatibility on *Poncirus trifoliata* to date, unlike other 'Eureka' lemon clones. Additionally, seeds are virtually absent in fruit of 'CE-D5-1-9-42', unlike fruit of other 'Eureka' clones, such as 'Cook Eureka'.

DESCRIPTION OF THE FIGURES

The accompanying photographs (as shown in FIGS. 1-6B) illustrate the overall appearance of the new lemon cultivar 'CE-D5-1-9-42'. These photographs show the colors as true as can be reasonably obtained in colored reproductions of this type. Colors in the photographs may differ slightly from the color values cited in the detailed botanical description, which accurately describe the colors of the new lemon cultivar.

DETAILED BOTANICAL DESCRIPTION OF THE CULTIVAR

Figure 1:
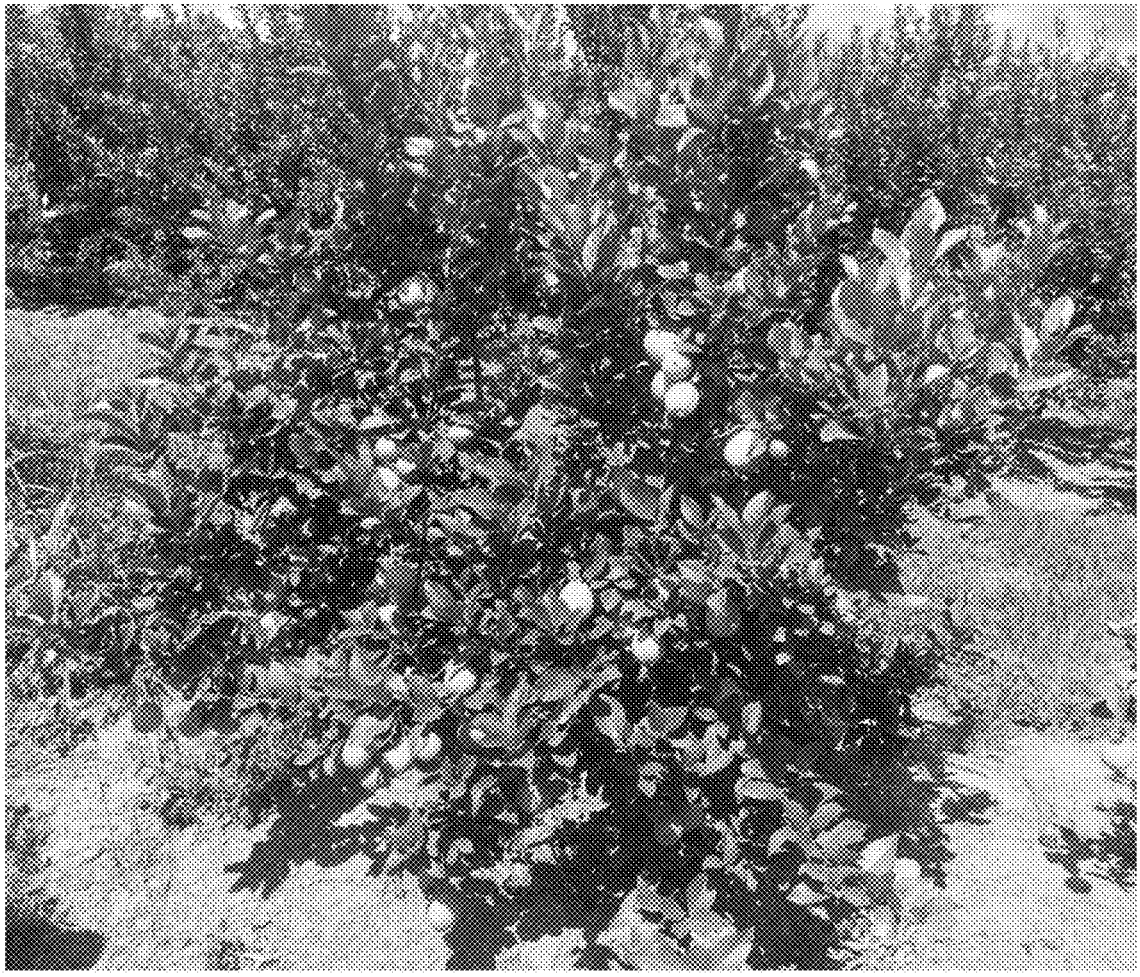
FIG. 1 shows a three-year-old tree of the new lemon cultivar 'CE-D5-1-9-42' growing on 'Flying Dragon' rootstock in South America, with no HLB.
Figure 2A:
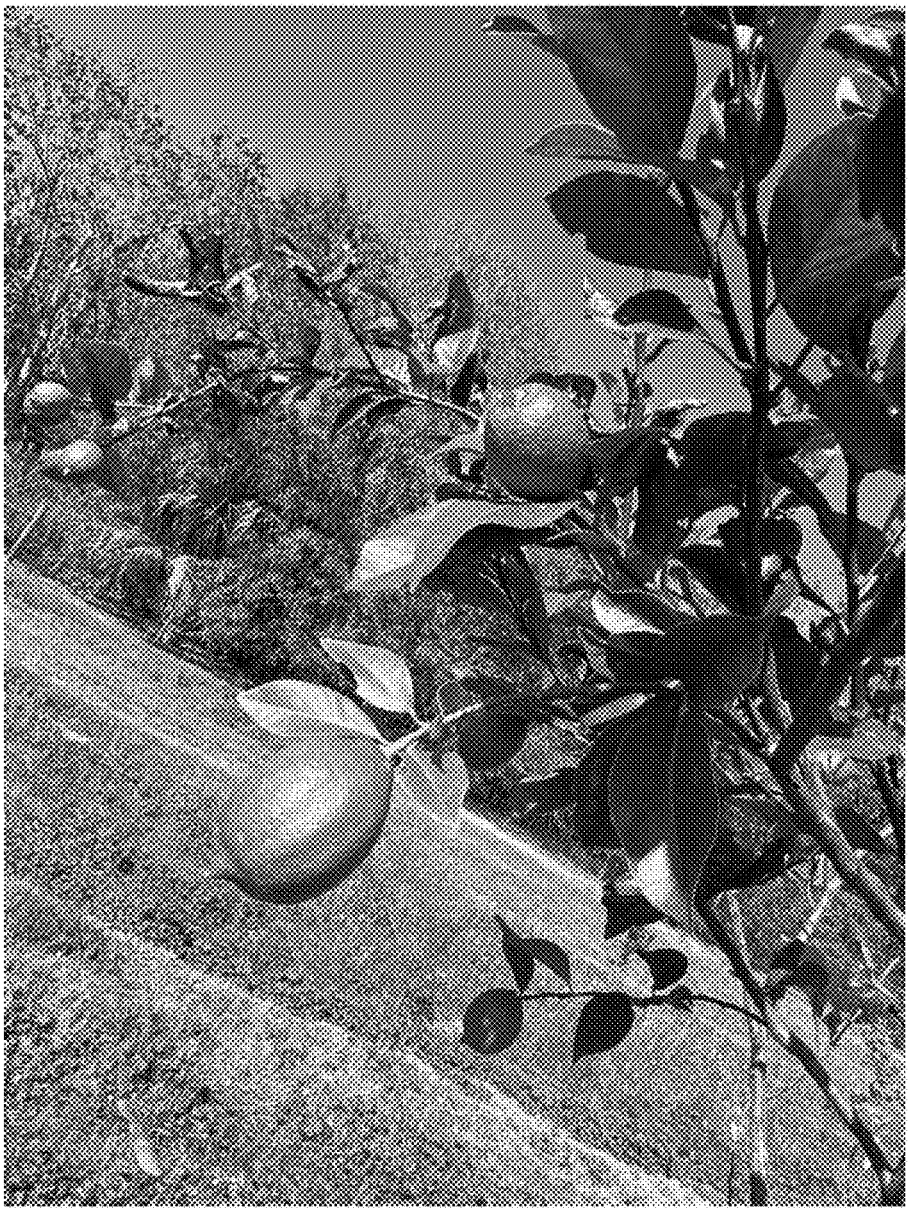
FIG. 2A shows a 2.5-year-old tree of the new lemon cultivar bearing fruit of various sizes, growing in Florida in the spring season.
Figure 2B:
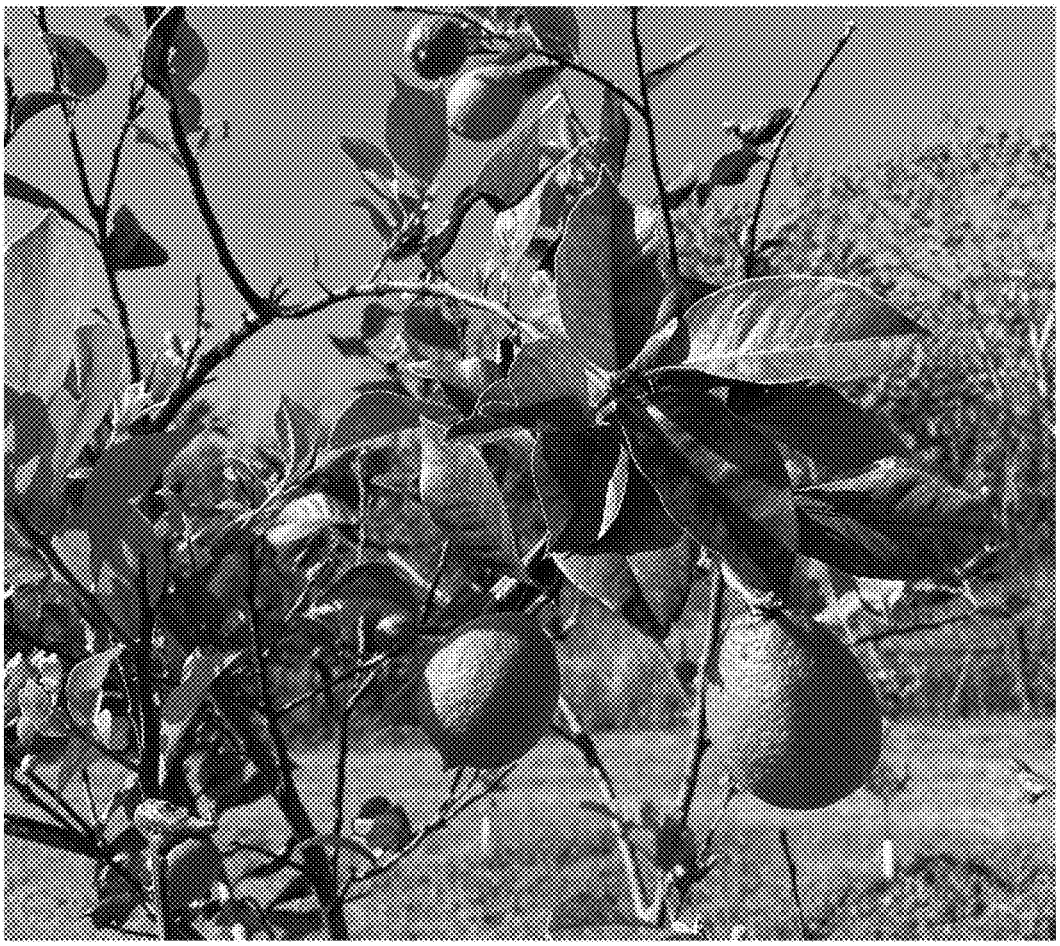
FIG. 2B shows the 2.5 year-old tree of the new lemon cultivar of FIG. 2A, bearing fruit and newly opened flowers.
Figure 2C:
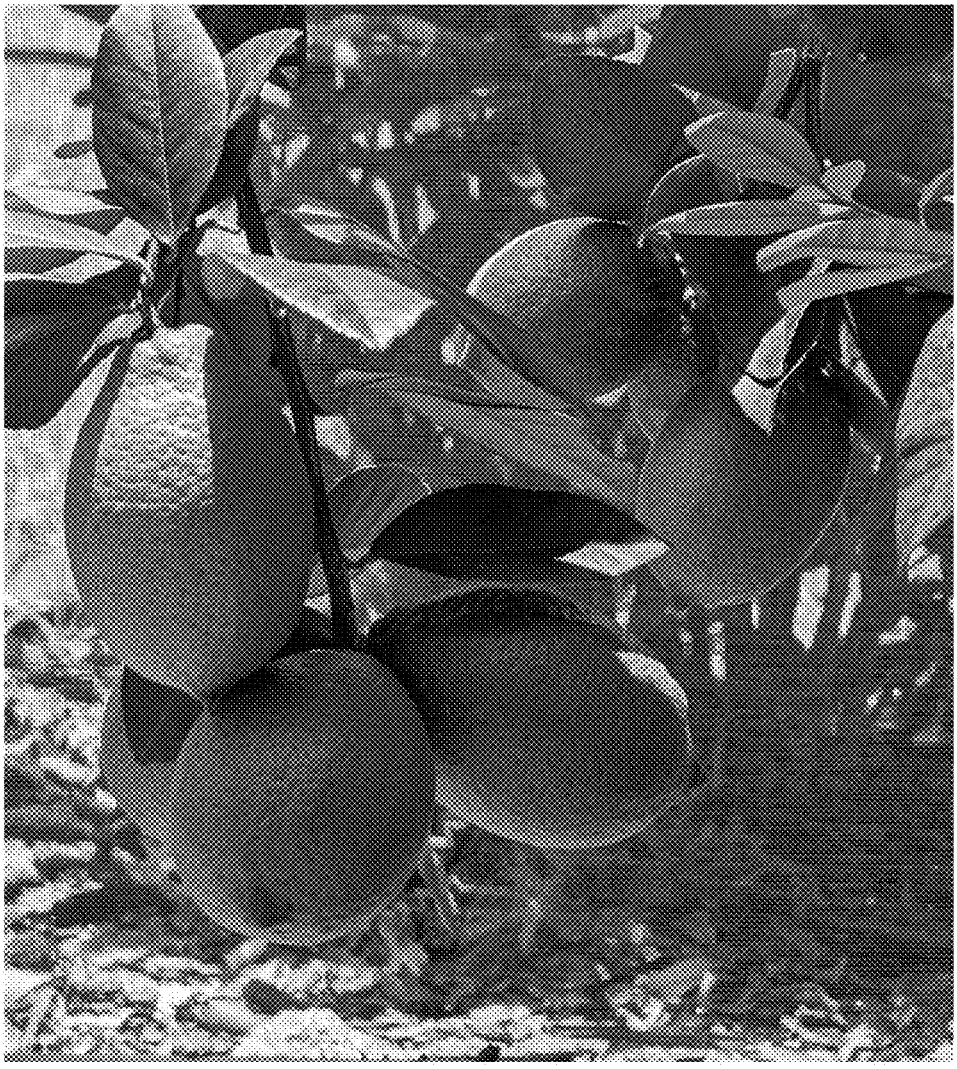
FIG. 2C shows clusters of fruit approaching maturity on a 2-year-old potted tree of the new lemon cultivar.
Figure 3A:
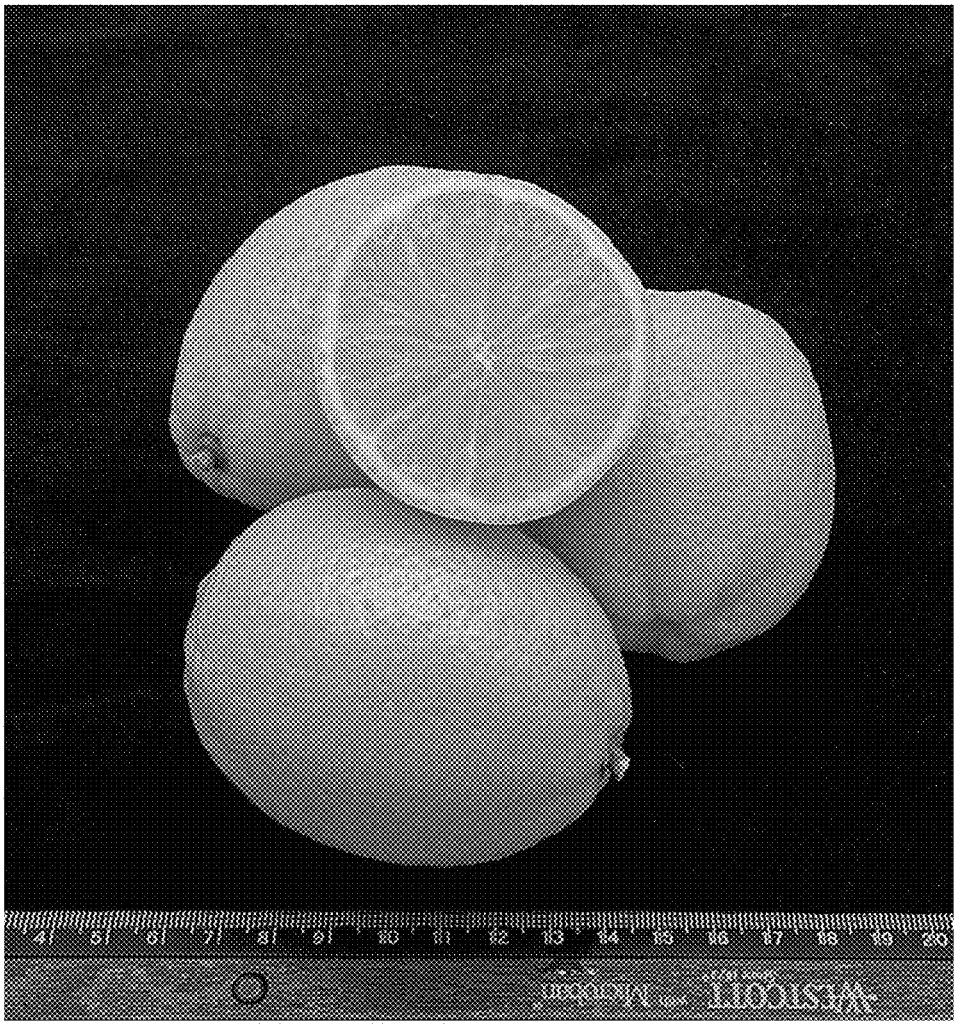
FIG. 3A shows whole and cut mature fruit of the new lemon cultivar.
Figure 3B:
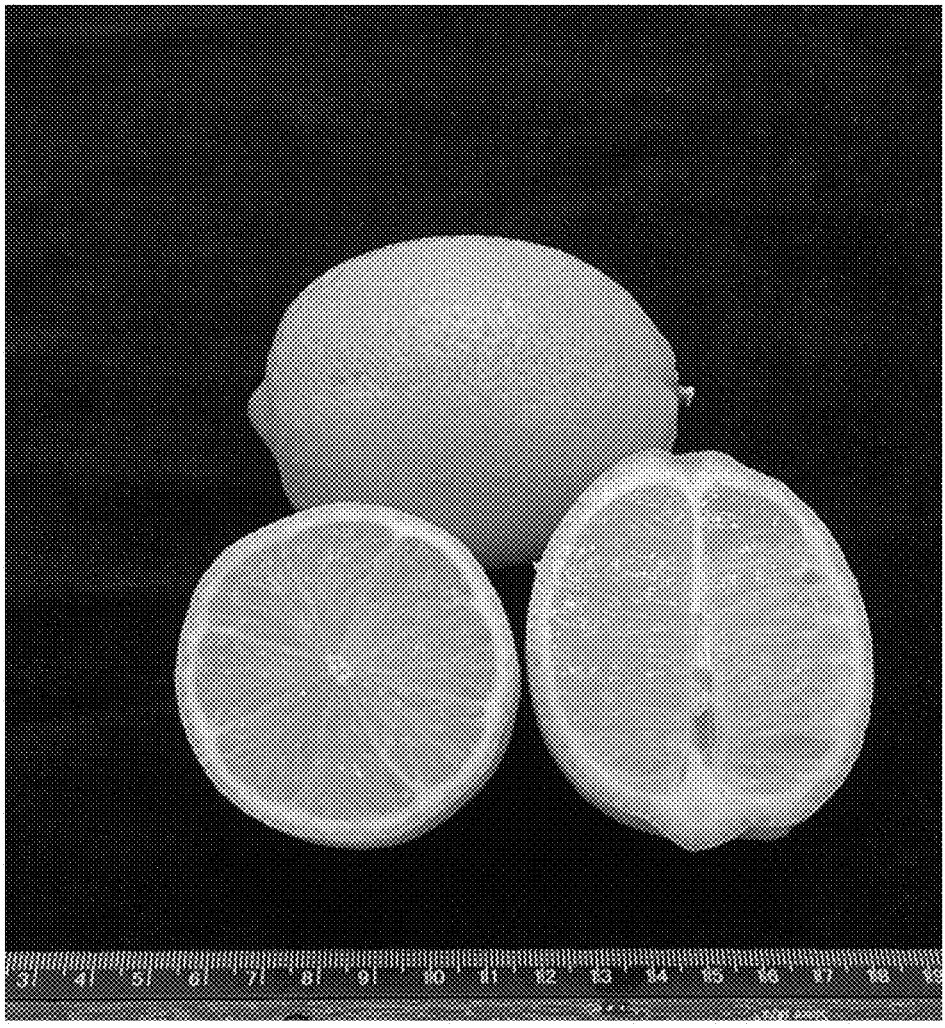
FIG. 3B shows whole and cut mature fruit of the new lemon cultivar.
Figure 3C:
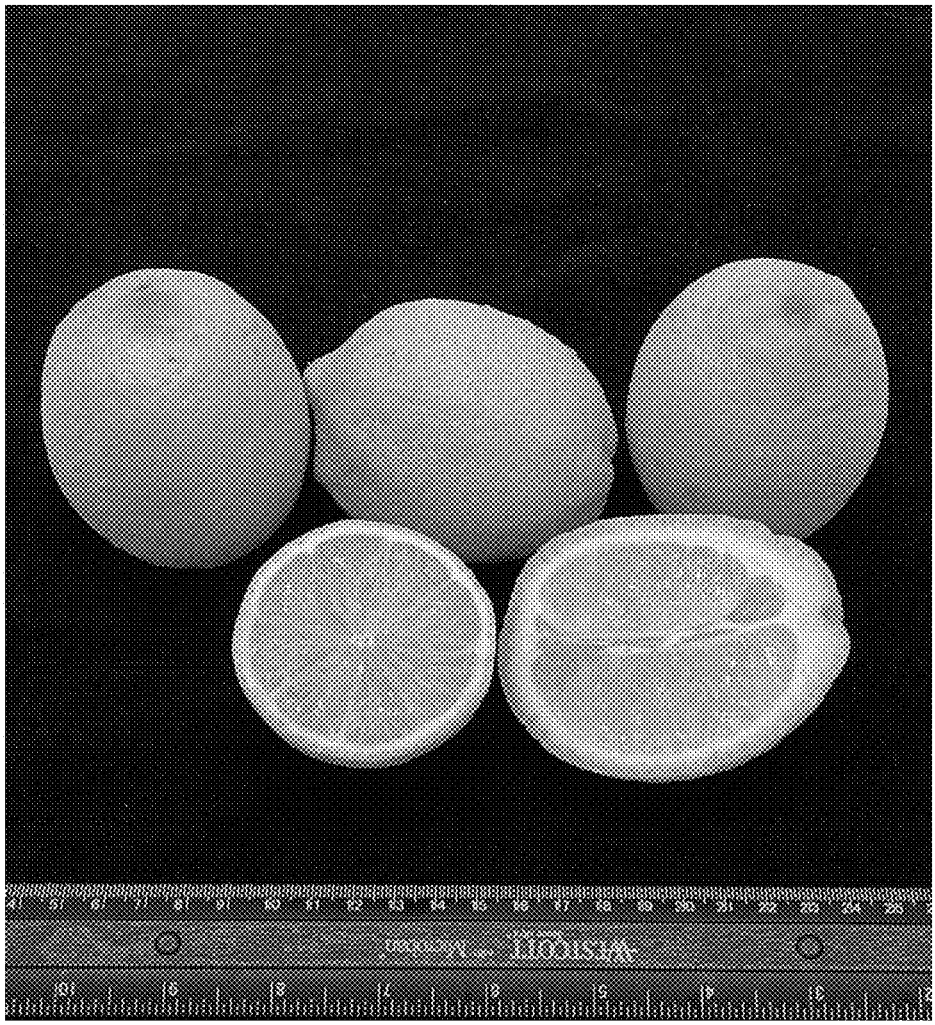
FIG. 3C shows whole and cut mature fruit of the new lemon cultivar.
Figure 3D:
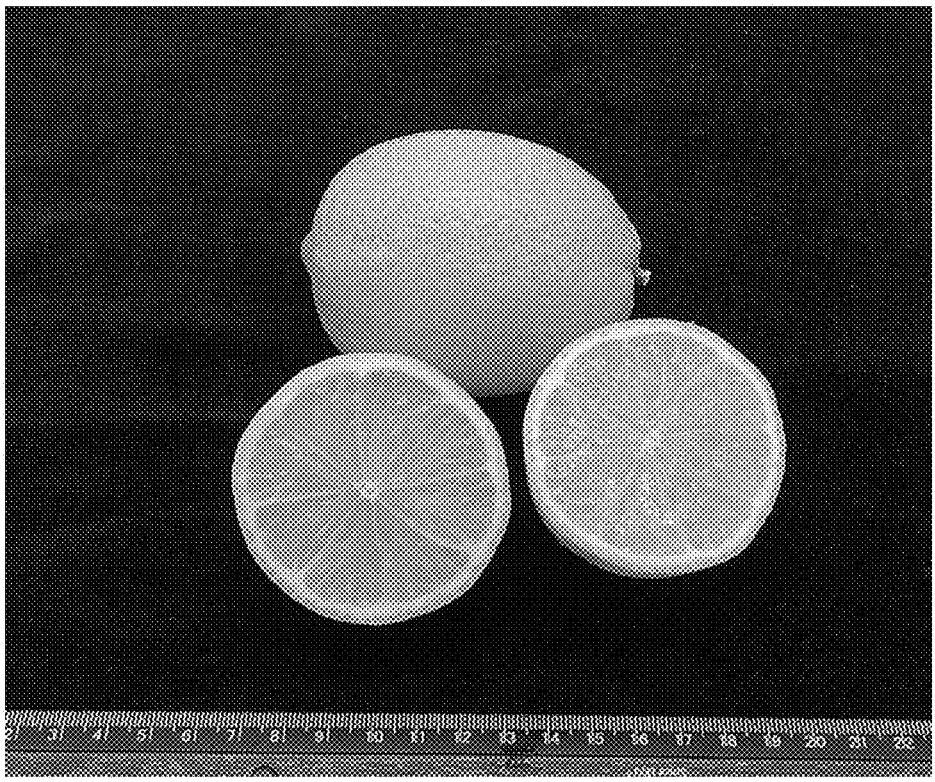
FIG. 3D shows whole and cut mature fruit of the new lemon cultivar.
Figure 3E:
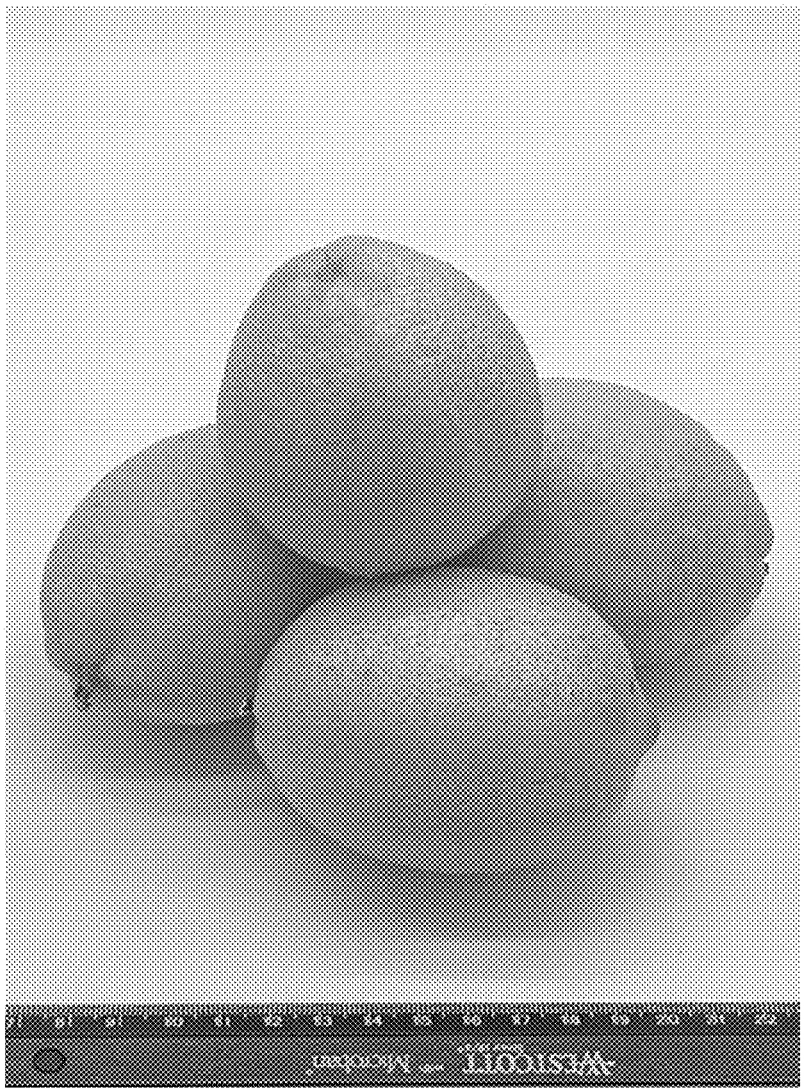
FIG. 3E shows whole mature fruit of the new lemon cultivar.
Figure 4A:
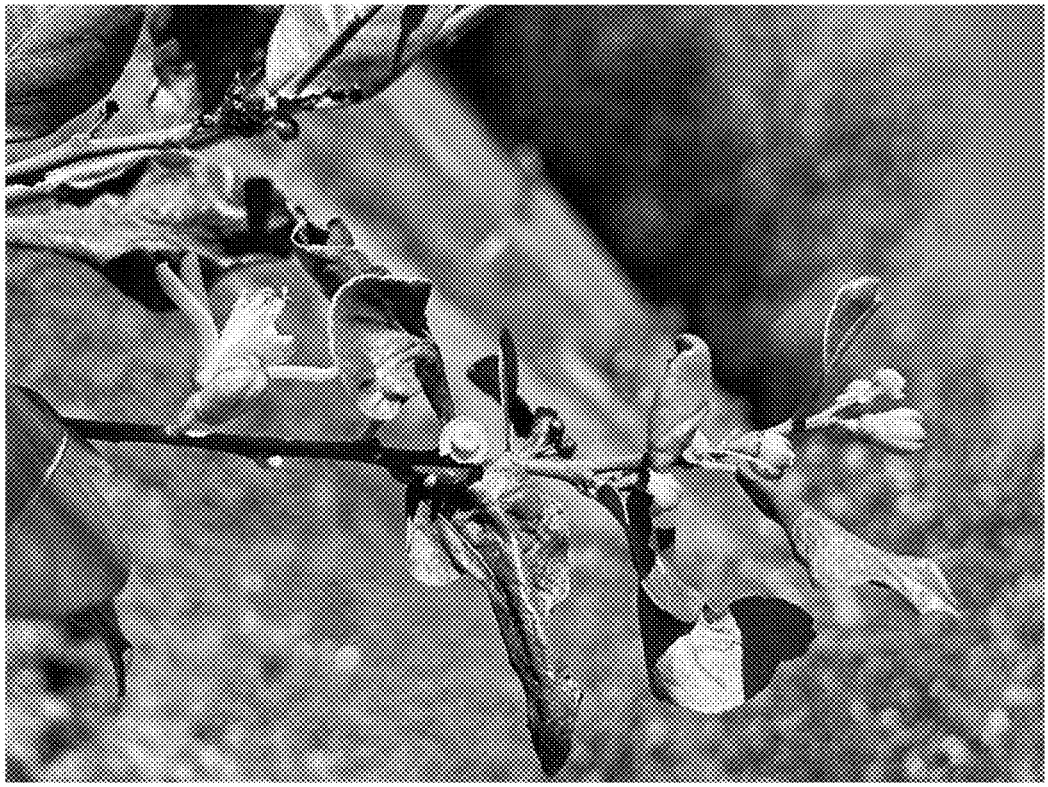
FIG. 4A shows flower buds and flowers on a 2.5-year-old tree of the new lemon cultivar.
Figure 4B:
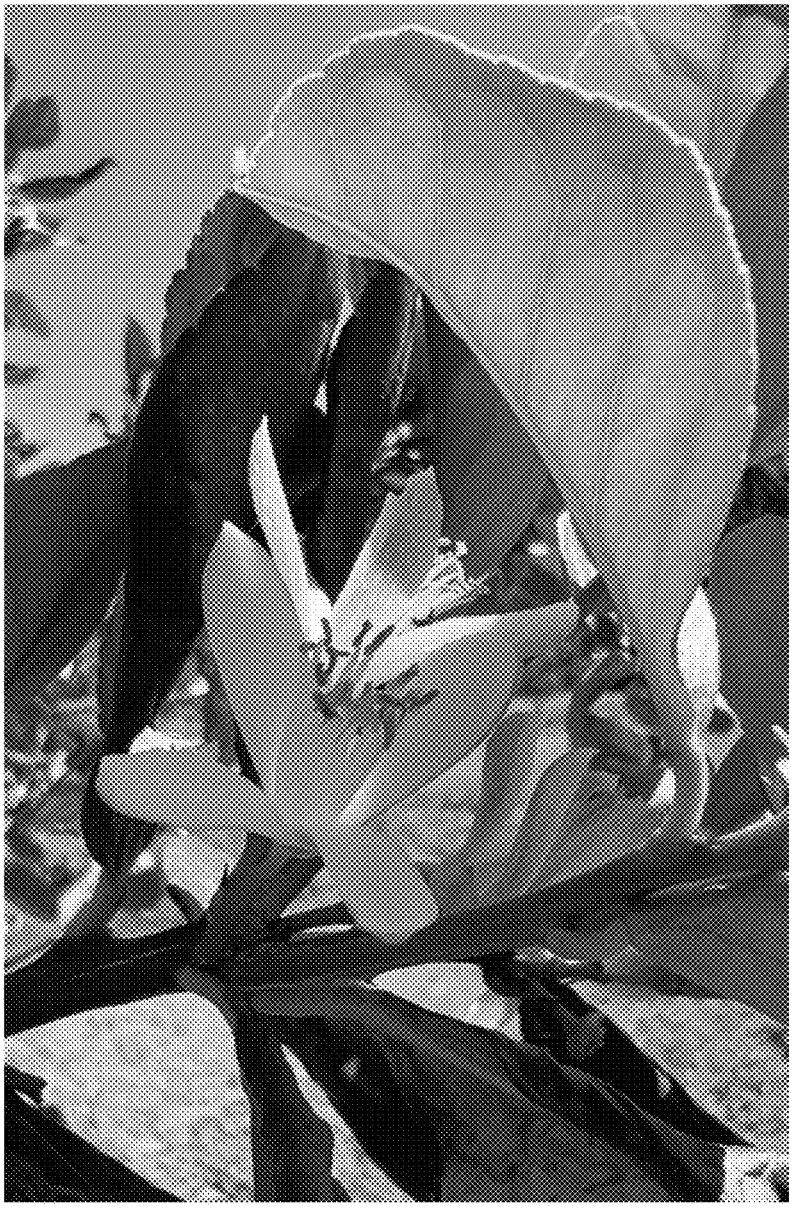
FIG. 4B shows flowers on a 2.5-year-old tree of the new lemon cultivar.
Figure 4C:
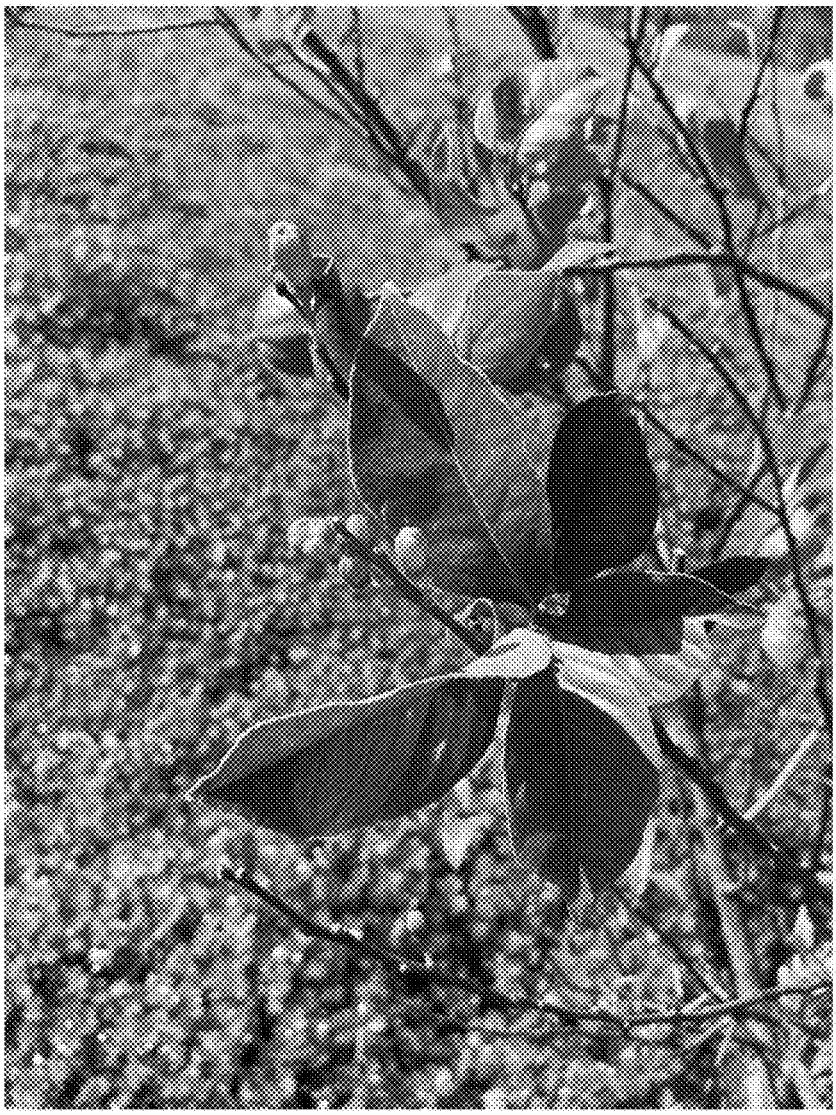
FIG. 4C shows flower buds on a 2.5 year-old tree of the new lemon cultivar.
Figure 4D:
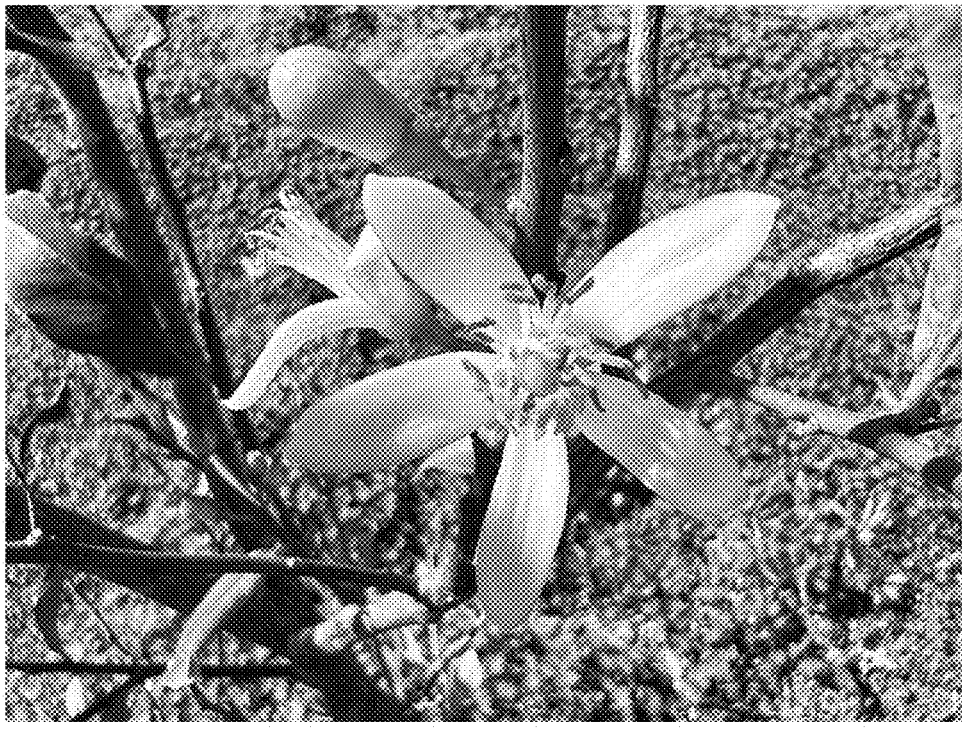
FIG. 4D show flower buds and flowers on a 2.5 year-old tree of the new lemon cultivar.
Figure 5A:
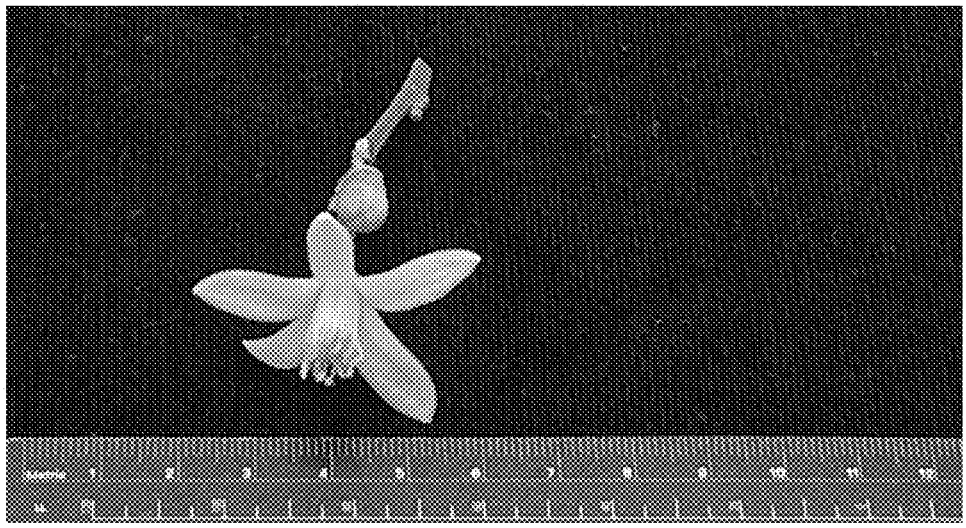
FIG. 5A shows a flower and a flower bud of the new lemon cultivar alongside a ruler for measurement.
Figure 5B:
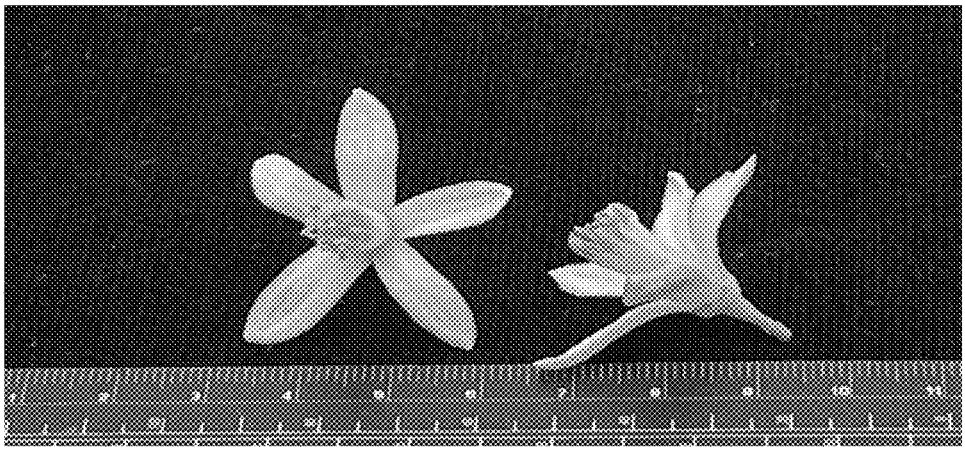
FIG. 5B shows flowers of the new lemon cultivar alongside a ruler for measurement.
Figure 5C:
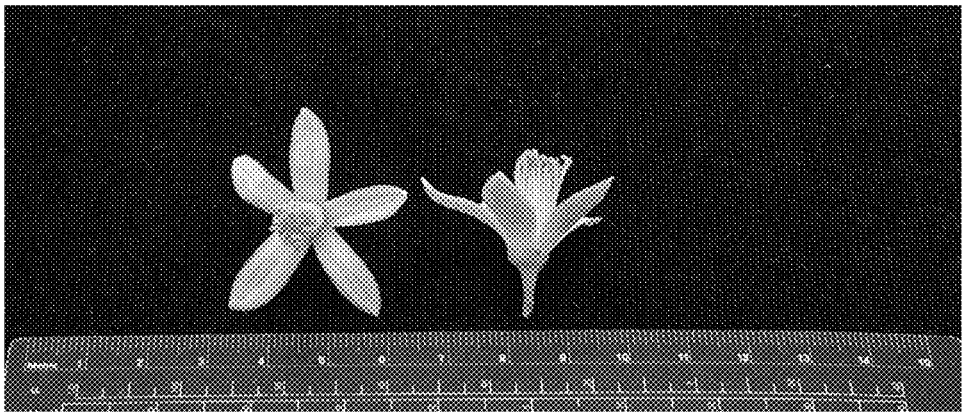
FIG. 5C shows flowers of the new lemon cultivar alongside a ruler for measurement.
Figure 5D:
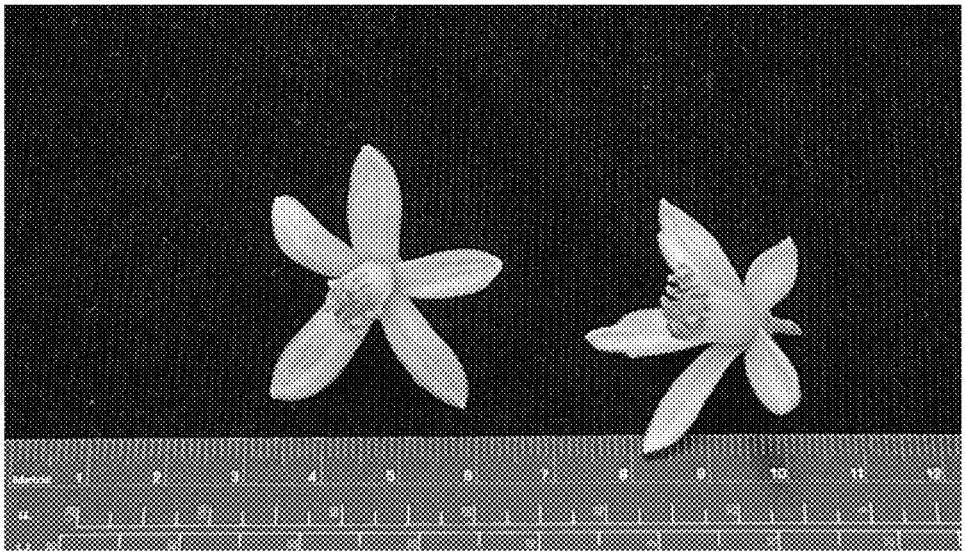
FIG. 5D shows flowers of the new lemon cultivar alongside a ruler for measurement.
Figure 5E:
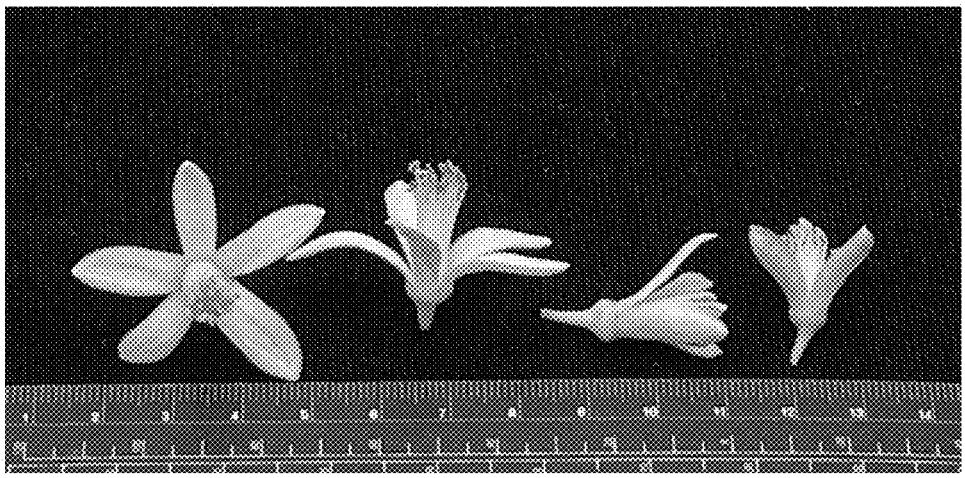
FIG. 5E shows flowers of the new lemon cultivar alongside a ruler for measurement.
Figure 5F:
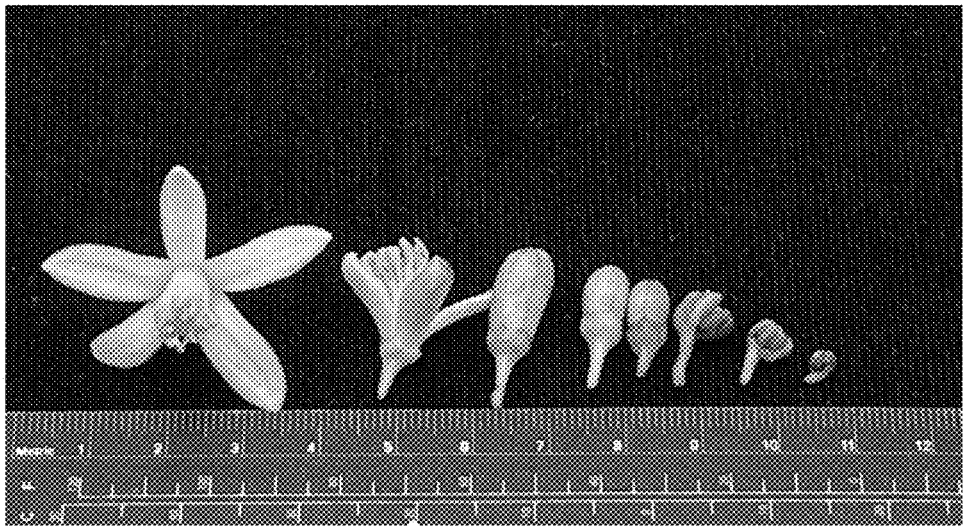
FIG. 5F shows flowers and flower buds of the new lemon cultivar in various stages of development alongside a ruler for measurement.
Figure 5G:
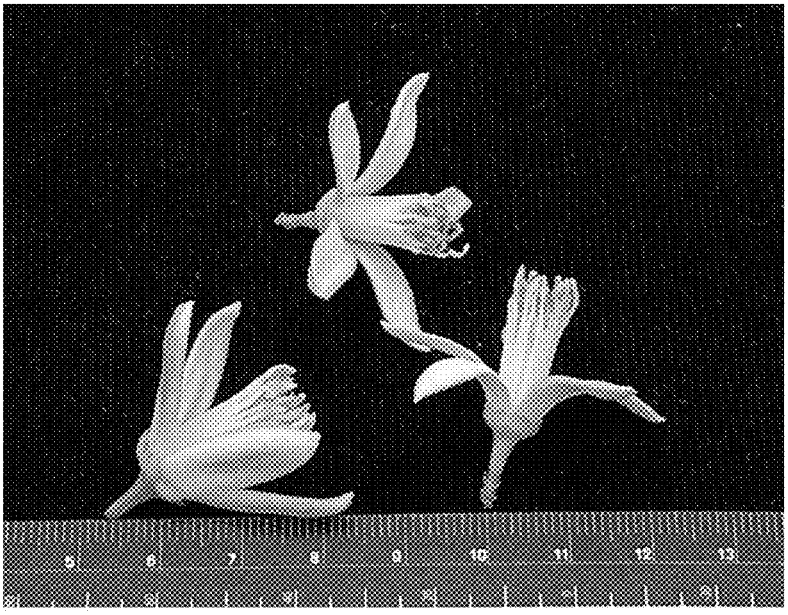
FIG. 5G shows flowers of the new lemon cultivar alongside a ruler for measurement.
Figure 5H:
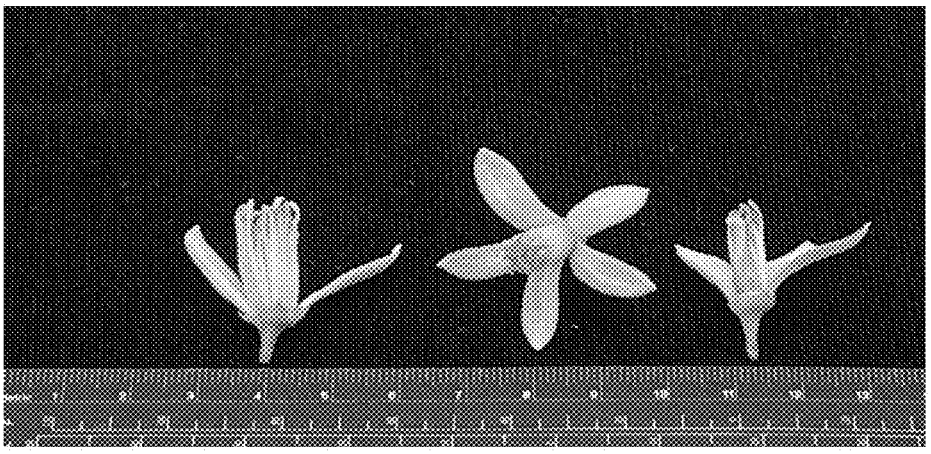
FIG. 5H shows flowers of the new lemon cultivar with a ruler for measurement, with some petals and stamen having been removed from the flower shown on the righthand side of FIG. 5H to reveal the stigma, style, and ovary.
Figure 5I:
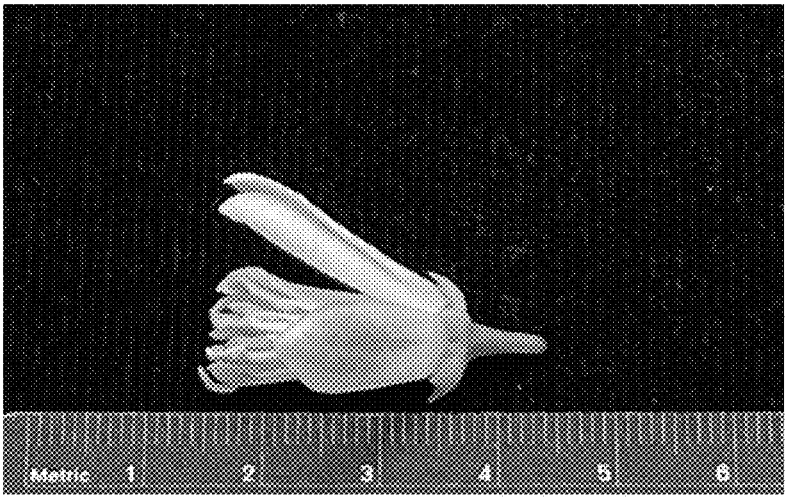
FIG. 5I shows a flower of the new lemon cultivar alongside a ruler for measurement.
Figure 5J:
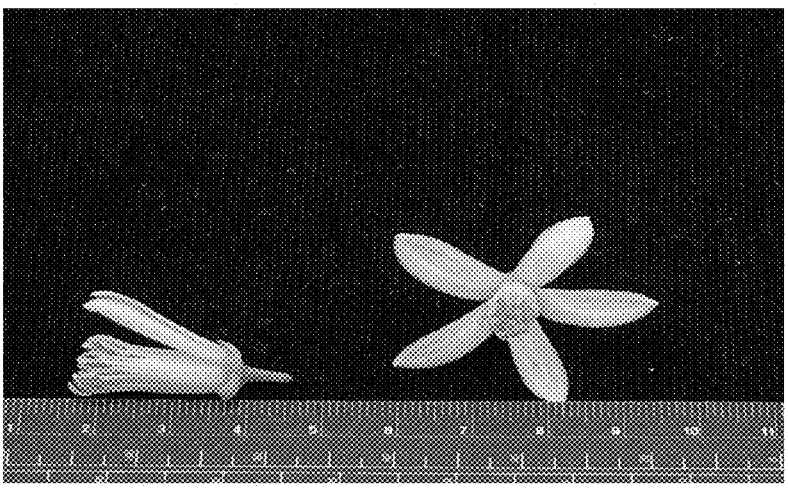
FIG. 5J shows flowers of the new lemon cultivar alongside a ruler for measurement.
Figure 6A:
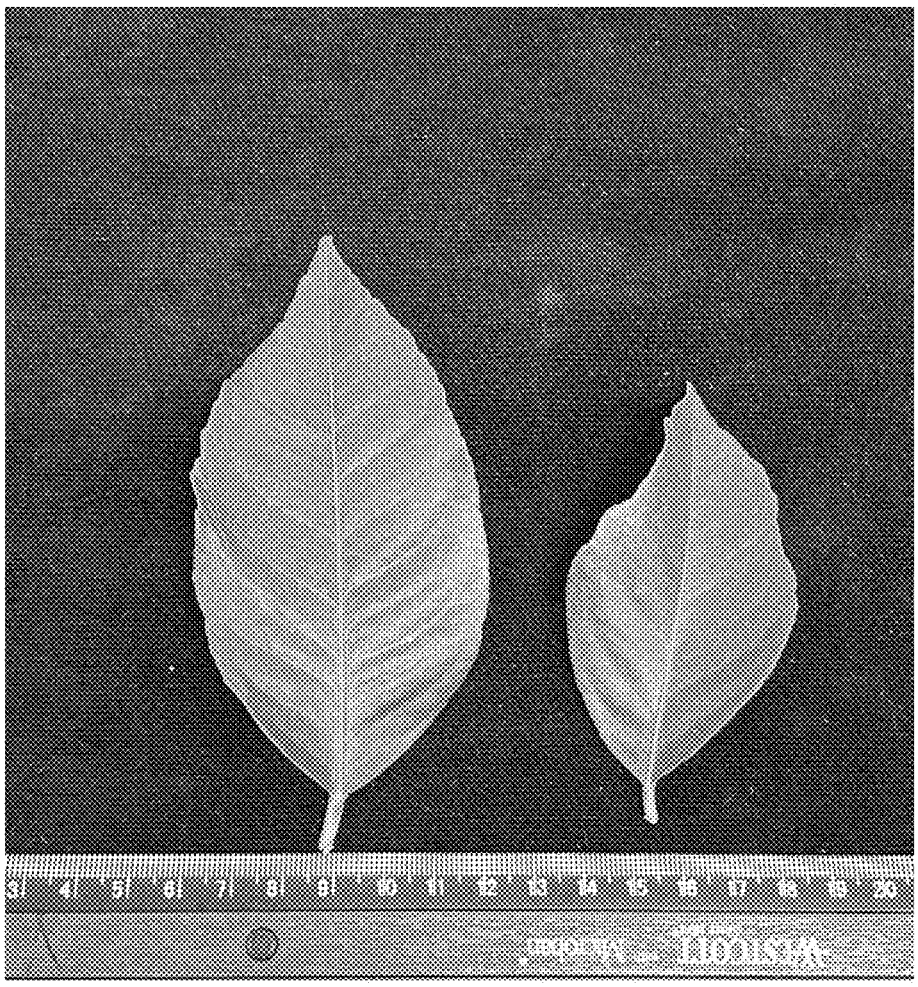
FIG. 6A shows fully expanded leaves of the new lemon cultivar alongside a ruler for measurement.
Figure 6B:
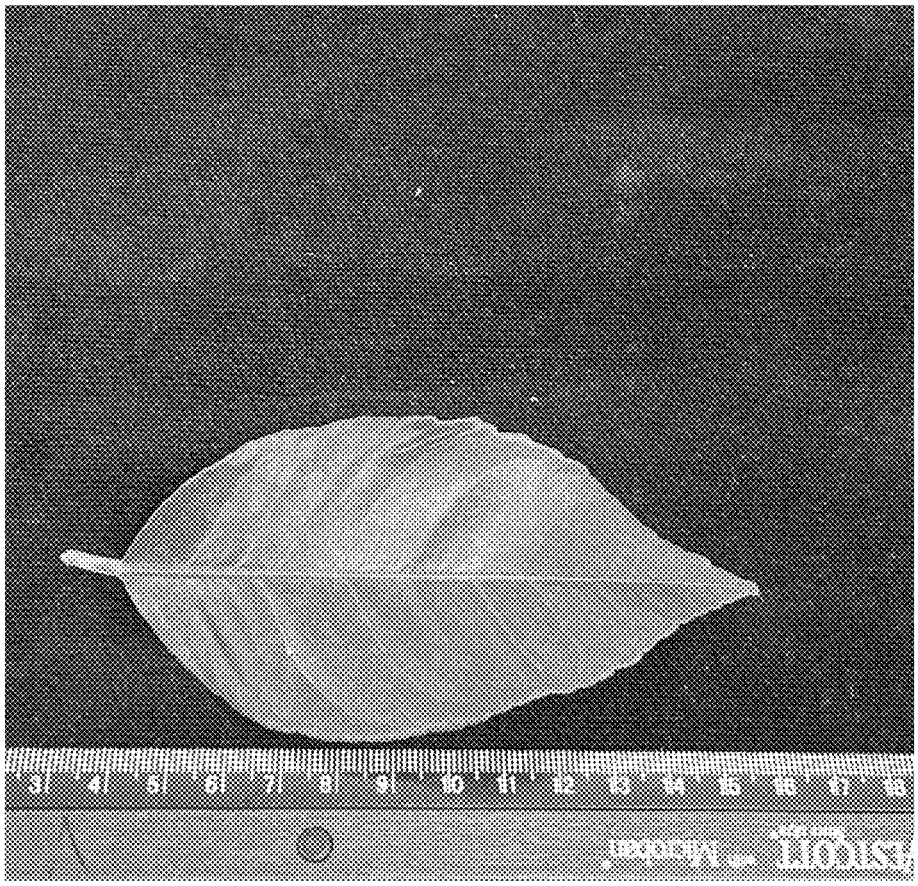
FIG. 6B shows a fully expanded leaf of the new lemon cultivar alongside a ruler for measurement.

In the following description, color references are made to The Royal Horticultural Society (R.H.S.) Colour Chart, 1986 Edition, except where general terms of ordinary dictionary significance are used.

BOTANICAL DESCRIPTION

Botanical classification:

*Family*.—Rutaceae.

*Botanical name*.—*Citrus limon* (L.) Burm.

*Common name*.—Lemon.

*Cultivar*.—'CE-D5-1-9-42'.

Parentage: The new lemon variety 'CE-D5-1-9-42' arose as an irradiated budwood clone from 'Cook Eureka' lemon.

Tree:

*Ploidy*.—Diploid.

*Size*.—Medium compared to the tree age (young tree).

*Width across row*.—1.5 meters on average.

*Width down row*.—1.4 meters on average.

*Tree height*.—2.1 meters on average.

*Tree canopy diameter*.—1.7 meters on average.

*Vigor*.—Moderate.

*Density*.—Canopies are moderately dense.

*Tree shape* (*form*).—Oblate shape (obloid).

*Growth habit* (*current season*).—Vegetative growth in general is moderate to vigorous. Growth habit is upright, typical for lemon trees.

Trunk:

*Trunk diameter*.—Approximately 4.5 cm at 30 cm above the ground.

*Trunk texture*.—Medium rough.

*Trunk bark color*.—RHS N200B (Brown Group).

Branches:

*Branch length*.—1.3 meters on average.

*Branch diameter*.—1.8 cm on average.

*Crotch angel.*—75-80 degrees on average (acute with an angle of less than 90 degrees).

*Branch texture.*—Relatively rough with long spines.

*Branch color.*—RHS 200D (Brown Group).

*Spine size.*—Approximately 3.5 cm in length and approximately 3.5 mm in diameter.

*Spine color.*—RHS N199A (greyed brown), with some being RHS 139B (green), depending on the branch age.

Leaves:

*Size* (*lamina average*).—Length: 110 mm on average. Width: 65 mm on average. L/W ratio: 1.7 on average. Thickness: Regular and average for lemon. Type: Simple (unifoliate). Shape: Elliptical. Apex: Acute to acuminate. Base: Acute to obtuse. Margin: Entire to undulate. Surface: Upper surface: Smooth. Lower surface: Medium veins that are pinnately netted. Color: Upper surface (adaxial): RHS N 137B (Green Group). Lower surface (abaxial): RHS 143C (Green Group). Petiole: Shape and attachment: Brevipetiolate; shorter than the leaf lamina. The junction between the petiole and the lamina is articulate. Shape (petiole wing): Obovate with narrow end at the base. Length: 15 mm on average. Width: 2.5 mm on average. Color: RHS 137B (Yellow-Green Group).

Flowers:

*Type.*—Perfect and staminate.

*Flower bearing.*—Single or cluster. If borne in clusters, each cluster consists of 2-5 flowers. If borne individually, individual flowers grow from leafy terminals and leaf axillaries.

*Flower diameter.*—Fully open flower has an average diameter of 32 mm.

*Flower depth.*—15 mm on average.

*Flower blooming period.*—Trees have a major bloom season in central Florida that can begin in early January. However, trees will bloom sporadically throughout the year, depending on environmental influences (cold weather and drought will stimulate additional flowering). First bloom: January. Full bloom: February.

*Fragrance.*—Flowers are very fragrant, with a lemon-like aroma.

*Flower bud size.*—Length: Approximately 2 mm for the initial visible flower bud; approximately 22 mm for the mature flower buds before opening. Diameter: Approximately 2 mm in the initial visible flower bud; approximately 7 mm in the mature bud. Flower bud shape: Initial visible flower bud with round dome shape; mature flower bud with elongated olive shape.

*Flower bud color.*—RHS 186B (Greyed-Purple Group) for the initial visible flower bud; RHS 186D (Greyed-Purple Group) mixed with RHS NN 155B (white) for mature buds.

Reproductive organs:

*Petals.*—Number: 5. Petal length: 25 mm on average. Petal width: 8 mm on average. Petal shape: Flat spatula shape. Apex shape: Smooth with obtuse angle. Base shape: Obtuse. Petal Color: Upper Surface: RHS 186D (Greyed-Purple Group) mixed with RHS NN 155B (white). Lower surface: RHS NN 155B (White Group). Margin: Smooth.

*Sepals.*—Number (per flower): 5. Shape: Delta shaped with acute angle at apex, although some with flat angle. Length: 4 mm on average. Width: 3 mm on average. Apex shape: Acute angle at apex. Margin: Smooth. Color: Upper surface: RHS 157B (green-white) with RHS 186D (Greyed-Purple Group) areas. Lower surface: RHS 157A (green-white).

*Pedicel.*—Length: 10 mm on average. Diameter: 2 mm on average. Color: RHS 144B (Yellow Group).

*Stamen.*—Number: 32 per flower on average. Length: 20 mm on average.

*Anther.*—Length: 4 mm on average. Width: 2 mm on average. Color: RHS 10A (yellow). Pollen color (general): RHS 11A (yellow). Pollen amount: Pollen is scarce.

*Pistil* (*in perfect flowers only*).—Number: 1. Length: 15 mm on average. Color: RHS 154D (yellow green). Style length: 16 mm on average. Style diameter: 2 mm on average. Style color: RHS 144A (yellow green). Ovary shape: Oval shape. Ovary diameter: 3 mm on average. Ovary color: RHS 142B (green).

Fruit:

*Size.*—Not necessarily uniform. In general, it is elongated oval to oval shaped with a neck that varies in size.

*Average weight* (*per individual fruit*).—97 grams on average.

*Length.*—7 cm on average.

*Diameter.*—6 cm on average.

*Shape.*—Oval to elongated oval with elongated tip. Broadest part of the fruit is at the middle.

*Shape* (*cross-section*).—Round.

*Apex.*—Prominently bulged, nipple-like shape on many fruit. Presence of nipple: Frequently present.

*Base.*—Short neck. Length of neck: Variable, 0.0-0.2 cm on average.

*Harvest.*—Date of first pick: Late May to late July from main bloom. Date of last pick: Can be harvested periodically throughout the year, depending on juice percentage, peel color, etc.

*Fruit stem.*—Length: 15 mm on average. Diameter: 4.5 mm on average. Color: RHS 146A (yellow green).

Rind:

*Adherence.*—Albedo (mesocarp) to flesh (endocarp) is medium to strong.

*Thickness.*—Medium (4 mm on average).

*Texture.*—Firm with excellent flavor.

*Surface texture.*—Smooth to slightly bumpy.

*Surface glossiness.*—Weak glossiness.

*Color.*—Flavedo (epicarp): RHS 146B (Yellow-Green Group). Albedo (mesocarp): RHS NN155C (White Group).

*Style end.*—Closed.

*Rind oil cell density.*—70-75 cell/square cm.

*Oil gland size.*—1.5 mm on average.

Flesh:

*Number of segments.*—8-9.

*Segment length.*—6.5 cm on average.

*Segment width.*—2.5 cm on average.

*Juice.*—Abundant.

*Color.*—RHS 146C (yellow green).

*Texture.*—Soft to medium.

*Vesicles.*—Medium thickness. Length: 10 mm on average. Diameter: 2.5 mm on average.

*Juice quality*.—Brix: 6.8. Acidity (average): 4.2%. Ratio: 1.6. Juice color: 29.

Seeds:

*Type*.—Seedless (observed seed count is 0-2 seeds per fruit, with the presence of seeds being rare).

*Seed shape, when found*.—Ovoid pointed.

*Seed polyembryony, when found*.—Seeds, when present, are polyembryonic.

*Fruit parthenocarpy*.—Yes.

What is claimed is:

1. A new and distinct lemon plant named 'CE-D5-1-9-42' as illustrated and described herein.

* * * * *